United States Patent

Ward et al.

[11] 4,008,289
[45] Feb. 15, 1977

[54] ADSORBENT TREATING METHOD

[75] Inventors: Dennis J. Ward, South Barrington; George R. Winter, III, Des Plaines, both of Ill.

[73] Assignee: Universal Oil Products Company, Des Plaines, Ill.

[22] Filed: July 7, 1975

[21] Appl. No.: 594,142

[52] U.S. Cl. .............................. 260/671 R; 203/41; 203/100; 208/188; 208/310 R; 208/310 Z; 208/321; 260/674 A; 260/674 SA
[51] Int. Cl.² .......................................... C07C 7/12
[58] Field of Search ..... 260/671 R, 674 A, 674 SA; 208/310 R, 310 Z, 321, 188; 203/41, 100

[56] References Cited

UNITED STATES PATENTS

| | | | |
|---|---|---|---|
| 2,323,524 | 7/1943 | Downs | 208/188 |
| 2,470,339 | 5/1949 | Claussen et al. | 208/310 R |
| 2,589,981 | 3/1952 | Weeks | 260/674 SA |
| 2,964,465 | 12/1960 | Brown et al. | 260/674 SA |
| 3,470,087 | 9/1969 | Broughton | 208/321 |
| 3,631,122 | 12/1971 | Berger | 260/671 R |
| 3,726,792 | 4/1973 | Francis et al. | 208/310 Z |
| 3,894,090 | 7/1975 | Cleveland | 260/674 A |
| 3,917,733 | 11/1975 | Winter | 260/674 SA |

*Primary Examiner*—D. Horwitz
*Assistant Examiner*—C. E. Spresser
*Attorney, Agent, or Firm*—James R. Hoatson, Jr.; Robert W. Erickson; William H. Page, II

[57] ABSTRACT

A more economical method of removing materials adsorbed on solid adsorbents used to treat hydrocarbon streams is presented. The method comprises removing a liquid hydrocarbon stream from a distillation column, vaporizing the liquid stream and superheating the vapors which are formed, passing the superheated vapor through the adsorbent and effecting the removal of the adsorbed material, and then returning the vapor to the fractionation column and utilizing the vapor as stripping media within the column. In the preferred embodiment, water is removed from alumina.

7 Claims, 1 Drawing Figure

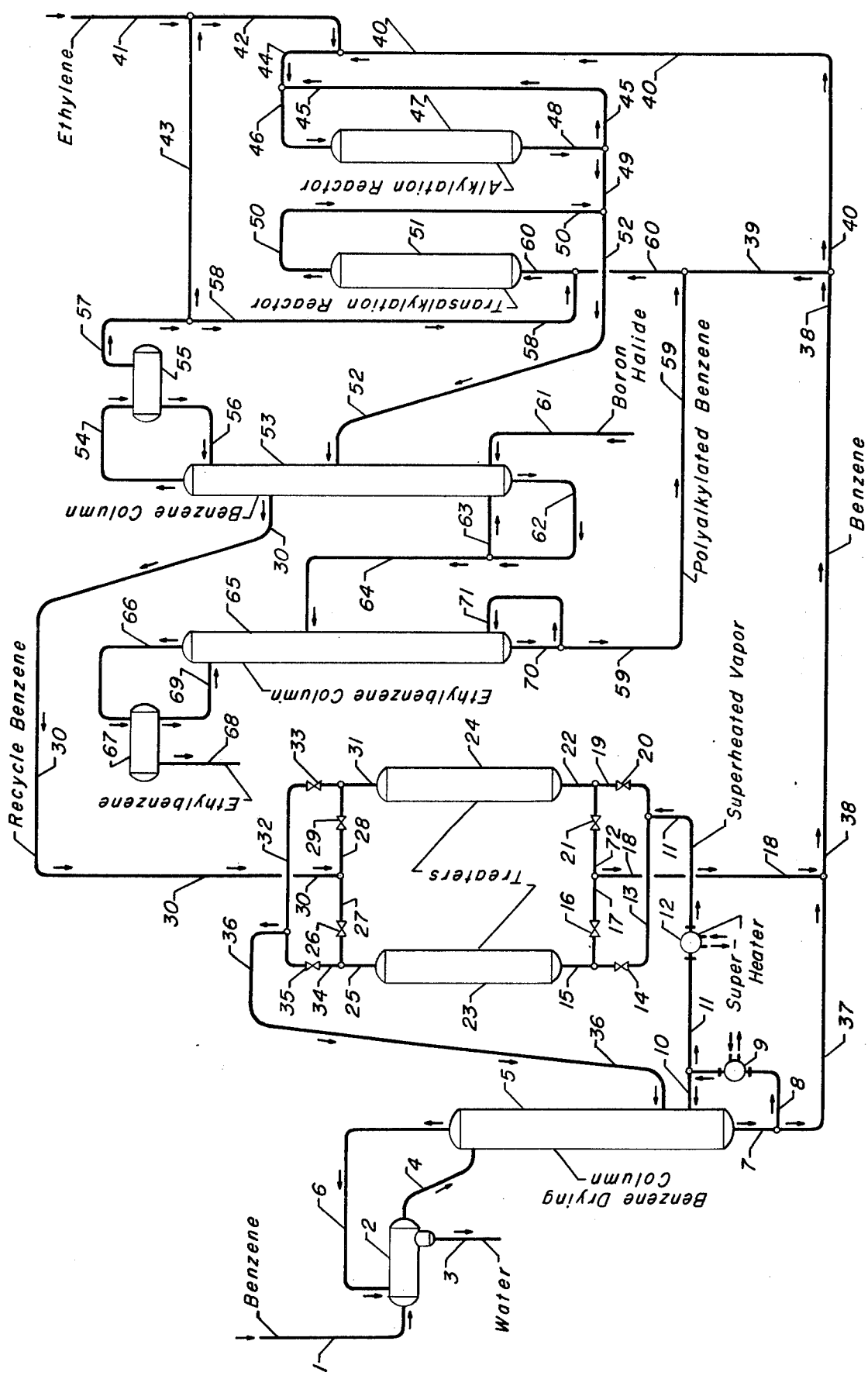

4,008,289

ADSORBENT TREATING METHOD

FIELD OF THE INVENTION

The invention relates to a method of removing an adsorbed material from a solid adsorbent such as alumina. The invention specifically relates to a method of drying a solid adsorbent, particularly one which is used to remove a borate-containing complex from a benzene recycle stream generated in a process for the alkylation of benzene which utilizes a boron halide promoted catalyst.

DESCRIPTION OF THE PRIOR ART

The use of solid adsorbents, such as alumina, to dry and treat various liquid and gaseous hydrocarbon streams is well established in the petroleum and petrochemical industries. The adsorbents are typically used to selectively remove undesired compounds for such purposes as feed preparation or by-product removal. In many of these situations, the treated stream should not be contaminated with water from the treating operation. It is therefore a part of the standard operating procedure of many treating units to effect a drying of the adsorbent prior to its use and to repeat this operation if regeneration is possible. The adsorbent is typically contained in a plurality of fixed beds which are used on a swing basis to provide continuous treatment capabilities. The operational sequence therefore comprises periodic removal of a particular treater from service and the replacement of the adsorbent and/or the subsequent drying of the adsorbent in this particular treater. Heretofore, the drying procedure has been performed with vapor streams specifically generated for the drying operation.

Various methods are established in the prior art which utilize internally generated streams, such as a portion of a product stream, to desorb material from an adsorbent. For instance, U.S. Pat. No. 3,063,934 (Cl. 208-91) describes a system wherein molecular sieves are used to remove benzene, olefins and sulfur from a feedstock charged to an isomerization process. This reference describes how a portion of the isomerate may be used to effectively desorb these contaminants from the sieves and thereby effect their regeneration. A somewhat similar process as applied to a reforming operation is described in U.S. Pat. No. 3,063,933. These references may be distinguished from the present invention by the fact that they are regeneration processes in which a contaminant is desorbed. In contrast, the present invention is a method of driving a material from an adsorbent which utilizes a superheated vapor and recaptures the energy content of this stream by injecting it as a vapor stream into a distillation column.

BRIEF SUMMARY OF THE INVENTION

The invention provides an improved method of drying or preparing beds of solid adsorbent used in the treatment of hydrocarbon streams. Specifically, the invention eliminates the necessity of generating a vapor stream which is used solely to dry or prepare the adsorbent. The steps involved in the practice of the invention include the removal of a liquid hydrocarbon stream from a fractionation column, the vaporization of the liquid hydrocarbon stream to effect the formation of a vapor stream, the superheating of at least a portion of the vapor stream and the contacting of the adsorbent with the superheated stream to effect the drying of the adsorbent, followed by the return of the vapor stream to the fractionation column as a stripping vapor fed to a lower portion of the column. From this description, it may be seen that the only equipment necessary for the drying operation, other than necessary valves and transfer lines, is a means to superheat the vapor.

DESCRIPTION OF THE DRAWING

The drawing illustrates the manner in which the preferred embodiment of the invention would be utilized in conjunction with a process for the alkylation of benzene to produce ethylbenzene.

A benzene feed stream enters the integrated process through line 1 and is passed into the overhead receiver 2 of a benzene drying column 5. The overhead vapor of the benzene drying column leaves the column through line 6, passes through the condensing means not shown and then enters the overhead receiver. Water is decanted from the overhead receiver through line 3, and a water-saturated benzene stream enters the benzene drying column through line 4. Dry benzene is removed from the bottom of the benzene drying column through line 7. A first portion of this material is diverted through line 8 and passed through a reboiler means 9. This effects the formation of a vapor stream which will normally pass through line 10 into the bottom of the benzene drying column in its entirety. When the invention is being utilized, a portion of the vapor stream formed in the reboiler 9 will be diverted through line 11 and passed through a superheater 12. This effects the formation of a superheated vapor stream which is passed through one of the two beds of adsorbent located in the treaters 23 and 24. For instance, when treater 23 is being regenerated, the stream of superheated vapor will pass through the open valve 14 in line 13 and then continue through line 15 into the treater 23. After passing through the adsorbent, the vapor stream will exit the treater through line 25, continue through open valve 35 in line 34 and be directed into line 36. This line carries the vapor stream to a lower portion of the benzene drying column where the latent heat of vaporization is utilized in the distillation operation. During this regeneration of treater 23, valve 33 in line 32 and valve 26 in line 27 located above the treaters and also valve 16 in line 17 and valve 20 in line 19 will all be in a closed position.

The net bottoms product of the benzene drying column is passed through line 37 and joins a stream of recycle benzene passing through line 18. The resultant benzene stream travels through line 38 to the point at which a first portion is diverted into line 39 and a second portion is directed into line 40. A stream of dry ethylene enters the process through line 41 and is admixed with a stream comprising boron trifluoride promoter in line 43 to form a gas stream traveling through line 42. This gas stream is admixed with the benzene stream which is traveling through line 40 to form the material passing through line 44. This material in turn is admixed with a recycle stream of the effluent of the alkylation reactor 47. There is thereby formed the net feed stream to the alkylation reactor, which passes into the reactor through line 46. The effluent of the alkylation reactor is removed through line 48 and divided into the portion recycled through line 45 and a second portion passed through line 49 to a fractionation zone. The benzene stream diverted through line 39 is admixed with a recycled stream of polyalkylated benzenes passing through line 59 to form the net hydrocarbon feed to a transalkylation reactor 51. This material passes through line 60 and is admixed with a vapor stream comprising the boron trifluoride promoter carried in line 58 and passed into the transalkylation reactor 51. The net effluent of this reactor is withdrawn through line 50 and combined with the material passing through line 49 to form the alkylation zone effluent.

The effluent of the alkylation zone is then passed into a benzene column 53 through line 52. A stream of a boron halide is passed into the bottom of the benzene column through line 61. The halide forms a volatile complex with boron oxide hydrates formed in the alkylation zone by the reaction of trace amounts of water in the olefin and hydrocarbon charge streams with the boron trifluoride circulated as a catalyst promoter. This hydrate-containing complex leaves the benzene column dissolved in a benzene recycle stream removed as a sidecut through line 30. The overhead vapor stream of the benzene column is removed through line 54 and passed through a condensing means not shown before being directed to the overhead receiver 55. The condensed hydrocarbons are returned to the benzene column as reflux through line 56, and the uncondensed vapors are removed through line 57 as the gaseous stream which contains the boron trifluoride promoter admixed with the feed stream to the alkylation and transalkylation reactors.

A stream of substantially benzene-free hydrocarbon material is removed from the benzene column 53 through line 62. A first portion of this is recycled through line 63 as material vaporized in a reboiler means not shown. The remaining net bottoms material passes through line 64 into an ethylbenzene column 65. Ethylbenzene is transferred upward and removed as the overhead vapor stream through line 66, and is then passed through a condenser means not shown and directed into the overhead receiver 67. A net product stream of relatively pure ethylbenzene is removed from the process through line 68 and a reflux stream is returned to the column through line 69. A bottoms stream comprising polyalkylated benzene is removed through line 70, with a first portion being diverted through a reboiler means not shown via line 71. The net bottoms product is then passed through line 59 to become part of the feed stream to the transalkylation reactor.

The recycle benzene stream removed in line 30 is directed into line 28 and passed through open valve 29 and then through line 31 into the treater 24. The solid adsorbent within the treater removes the boron-containing complex from the recycle benzene stream. This effects the formation of a purified benzene recycle stream which leaves the treater through line 22 and is directed through valve 21 in line 72 to the junction with line 18. The recycle benzene stream then continues through line 18 and is admixed with the feed benzene from the drying column passing through line 37 prior to being returned to the alkylation zone through line 38.

Those skilled in the art will recognize that this drawing has been simplified for the purposes of brevity and simplicity by the deletion of control systems, many necessary mechanical features and several minor subsystems, such as those used to remove tar from a drag stream of the polyalkylated benzenes and to regenerate the boron trifluoride catalyst promoter.

DETAILED DESCRIPTION

Solid absorbents are widely used in the petroleum and petrochemical industries for the selective removal of undesired compounds from gaseous and liquid streams. They are often used to remove inorganic materials such as halogen-containing compounds, nitrogenous materials, alcohols, organic acids, etc. These treaters are used on feed streams, recycle streams and effluent streams from these various processes. In a number of these applications, the adsorbent cannot be regenerated and must be replaced periodically. Furthermore, it is often required to dry or purify the adsorbent before it can be used. This may be because of the undesired effect of water or the impurities being removed on either the material being treated or a catalyst used within the process. For instance, in a hereinafter described alkylation process, treaters are used to remove a boron-containing complex from a benzene stream before its passage into an alkylation zone. The boron-containing complex is the result of an undesirable contaminant formed in the alkylation zone due to the presence of water. Another illustrative example may be found in treaters used in conjunction with a process wherein it is desired to minimize the water content of various streams as a means of reducing the rate of corrosion. Specifically, it would often not be desired to use a wet adsorbent in a process wherein the effluent of the treater was commingled with hydrofluoric acid. Treaters are also used to remove contaminants from the feed stream to isomerization units as it is also desired that these charge streams are as dry as possible. Finally, one of the common treatments performed by solid adsorbents is the drying of a hydrocarbon stream. In this case, the adsorbent functions as a desiccant and is normally regenerated at frequent intervals.

In the past, drying of adsorbents has been performed using an externally derived material which must be vaporized or heated prior to its usage and must then be disposed of after its usage. This normally entails the requirement for a separate heater, a dependable source for the material used, means to cool the effluent of the treater and some suitable place for its disposal or usage. It is an objective of this invention to provide an improved and more economical method of drying, treating or purifying the solid adsorbents used in hydrocarbon conversion processes.

By the process of this invention, this objective is obtained by utilizing a stream of material from the bottom of a fractionation column as the source of vapors used to dry the solid adsorbent. It may be seen that there is frequently already provided a reboiler which may be suitable for the generation of the vapor, and that this eliminates the need of any vapor generation apparatus. Furthermore, this vapor need only be superheated to the extent needed to raise its temperature to that desired for the drying operation. In comparison to the prior art, this equipment is normally minimal. As an alternate, any vapors generated in a separate vaporization means for this drying or purification step may be used to reduce the size of the column reboiler required. The used vapors removed from the treater are returned to the fractionation column and the latent heat of vaporization imparted in the vaporization step is therein utilized to perform the desired distillation. There is therefore a recovery of the energy imparted in the superheater which is not used in the treaters, and the recovery of any remaining superheat allows a corresponding reduction in the required reboiler duties. The invention also eliminates the need for any facilities to cool and dispose of the used vapors.

When used for water removal, the invention is best suited for usage with a fractionation column used to dry a hydrocarbon stream, since this provides an ideal point for the rejection of the water-containing vapors. Such a mode of operation is the preferred embodiment of the invention. A second specific embodiment of the invention is the removal of n-methyl pyrolidone from silica gel used to remove this material from a benzene stream. This nitrogenous material is used to purify the benzene and has a detrimental effect on acidic catalyst.

The process of the invention may be adapted for use in any operation with an adsorbent wherein it is desired to heat the adsorbent by a vapor in order to drive off undesired or adsorbed materials. It is therefore not intended to limit the invention to those specific examples set out herein. The invention may be practiced with any adsorbent which is beneficially effected by exposure to heated vapors. It is preferred that the solid adsorbent be a desiccant alumina but a great many other adsorbents may be substituted. For instance, other aluminas include active alumina, catalytic alumina, activated bauxite and chromatographic alumina. Materials other than alumina may be used as the adsorbent. These include the siliceous adsorbents such as aluminosilicates, acid-treated clay, magnesia-silica gel, fuller's earth, diatomaceous earth or silica gel. The various carbon-type adsorbents which may also be beneficially treated by the process of the invention include the shell-based, wood-based, coal-based or petroleum-based carbons. Furthermore, inorganic materials such as various resins may also be used as the adsorbent.

The conditions which must be imposed upon the adsorbent for the successful operation of the invention will vary with both the adsorbent used and the material which is to be removed from the adsorbent. The necessary conditions will also depend upon whether these materials are being retained by chemisorption or physical absorption. Those skilled in the art are already well informed about the necessary operating procedures, basically the temperature, which is required for the subject process since the present invention is an improvement on an already commercially practiced operation. In general, the absorbent is maintained at an elevated temperature sufficient to drive off the undesired materials. For instance, when desiccant alumina is being dried, the alumina is maintained at a temperature of from about 300° to about about 350° C. for a period of from about 4 to 24 hours.

In accordance with this description, a broad embodiment of the invention may be characterized as a method of removing an absorbed material from a solid absorbent used to treat liquid hydrocarbons which comprises the steps of withdrawing a liquid hydrocarbon stream from a fractionation column, vaporizing the liquid hydrocarbon stream and effecting the formation of a vapor stream, superheating the vapor stream, contacting the solid absorbent with the vapor stream and effecting the removal of the absorbed material from solid absorbent, and returning the vapor stream to the fractionation column as a stripping vapor fed to a lower portion of the fractionation column.

Practice of the invention requires the removal of material from the reboiler section of a fractionation column and its return to the fractionation column. It is not necessary that the column is one which acts upon a material passed through the treater or that the column is used in the same process as the treater. Since many commercial processes contain several fractionation columns, there will often be a choice available as to which column will be utilized. The first factor to be considered is the temperature of the vapors generated in the reboiler in comparison to the temperature required for the vapors passed into the treater. Preferably, there should be a minimum difference between these two temperatures in order that the amount of heat which must be added to the vapors can be minimized. A second and possibly controlling consideration, is that the material which is removed from the absorbent must be tolerable in the distillation column and its products.

The process for the alkylation of benzene illustrated in the drawing often has associated with it a distillation drying column used to dry the incoming benzene feed stream. However, this process may also be utilized to illustrate how the invention is adaptable for use with a different distillation column. Therefore, as an aid to understanding these two embodiments of the invention, a more detailed description of the alkylation process will now be provided.

The alkylation reaction is carried out in the presence of a boron halide promoted catalyst comprising a boron halide-modified inorganic oxide, such as alumina, and the boron halide. The halide is preferably boron trifluoride. This reaction is performed in an anhydrous alkylation promoting environment, but as a practical matter, completely anhydrous streams of charge stock are never available and a minute amount of water inevitably enters the system. As a result, there is formed in the alkylation zone a reaction product of water and the boron halide. This relatively non-volatile hydrate of boron oxide exits the alkylation zone in the alkylation zone effluent in a dissolved or suspended state. These hydrates are often referred to simply as borates. The alkylation zone effluent is then passed into a first distillation column commonly referred to as the benzene column. The unalkylated benzene is removed as a sidecut which is recycled, and alkylated aromatic benzenes are removed as a bottoms stream. The relatively non-volatile boron oxide hydrates will precipitate out and form insoluble deposits in the first distillation column unless corrective action is taken. These deposits may be prevented by passing a relatively pure boron halide into the lower portion of the first distillation column at a point below the level at which alkylation zone effluent stream enters the column. This halide forms a volatile complex with the non-volatile boron oxide hydrates, and the resultant boron containing complex is continuously removed from the column dissolved in the benzene stream. The benzene sidecut stream is then passed through treaters containing beds of alumina which selectively remove the complex and recycled to the alkylation zone. A detailed description of this commercial process is found in U.S. Pat. Nos. 3,631,122; 3,126,421 and 2,887,520.

The effluent of the alkylation zone is fed into the benzene column. This column is normally operated at a bottom pressure of about 2 atmospheres with about a 0.35 atmosphere pressure drop through the column. The liquid temperature at the bottom of the column will be about 177° C. to insure removal of the benzene from the alkylated benzenes being withdrawn. The temperature at the point of removal of the benzene sidecut will be about 99° C., and the top of the column will be maintained at about 93° C. The alkylated benzenes are separated in a second fractionation column called an ethylbenzene column, which is maintained at about 1.6 atmospheres pressure, a bottom temperature of about 208° C. and a top temperature of about 138° C.

The benzene feed stream to the process is normally fed into the overhead receiver of a distillation drying column to avoid upsetting the operation of the column when large surges of water are present in the feed stream. This drying column can be effectively operated at a pressure of about 1.3 atmospheres, a bottom temperature of about 105° C. and a top temperature of about 99° C. During operation, an overhead vapor stream of water and benzene is condensed, and the resulting liquid is collected in the overhead receiver, wherein the water and benzene form two distinct phases. The water is removed by decantation, and the now saturated benzene is returned to the column as reflux. Dry benzene is removed as the net bottoms product of the benzene drying column.

The alumina used to treat the benzene recycle stream must be regenerated or replaced when the weight percent of boron oxide hydrate reaches a limiting value of about 7 to 10 percent. Assuming replacement, the flow of the benzene recycle stream is directed into a different treater; the used alumina is removed and fresh alumina is placed in the treater. The spent alumina can, if possible, also be used to treat some other stream if it will still function for this purpose. The next step in the alumina replacement procedure is the drying of the alumina with superheated vapors generated by further heating of a portion of vapors generated in the reboiler of the benzene drying column. These vapors are superheated to a temperature of from about 300° to 350° C. The vapors leaving the treater are then returned to the benzene drying column and used as stripping vapor which provide heat to the column.

As an alternative method of applying the process of the invention, a portion of the vapors generated in the reboiler utilized on the ethylbenzene column may be superheated and used as the vapors which dry the alumina. In either of these modes of operation, the vapors which are returned to the fractionation column should enter that column at a point above the bottom of the column to prevent the contamination of the bottoms liquid with water. This is important because both bottoms streams are recirculated to the alkylation zone, and contamination of these streams with water would produce more of the undesired boron oxide hydrates. This precaution may not be necessary in other processes.

We claim as our invention:

1. A method of removing adsorbed material from a solid adsorbent in a process employing a fractionation column, which comprises the steps of:
   a. removing a liquid hydrocarbon bottoms stream from the lower portion of said column and reboiling the same to form vapors;
   b. returning a portion of said vapors to the lower portion of the column;
   c. superheating another portion of said vapors to a temperature sufficient to vaporize the adsorbed material from said adsorbent;
   d. contacting the superheated vapors with the adsorbent and thereby removing adsorbed material from the adsorbent; and
   e. supplying the resultant vapor stream to the lower portion of said fractionation column.

2. The method of claim 1 further characterized in that said adsorbed material comprises a hydrocarbon.

3. The method of claim 1 further characterized in that the adsorbent is alumina and the adsorbed material is water.

4. The method of claim 1 further characterized in that the liquid hydrocarbon bottoms stream comprises benzene.

5. The method of claim 1 further characterized in that the adsorbent is silica gel, the liquid hydrocarbon bottoms stream is benzene and the adsorbed material is N-methyl pyrolidone.

6. In a process for the alkylation of benzene wherein:
   a. benzene is passed into a benzene drying column to form a dry benzene feed stream;
   b. the dry benzene feed stream is reacted with an olefin in an alkylation zone containing a boron halide promoted catalyst, and an alkylation zone effluent comprising benzene, an alkylaromatic hydrocarbon and boron oxide hydrates is removed from the alkylation zone and passed into a fractionation zone;
   c. the formation of a volatile complex containing the boron oxide hydrate is effected by admixing the boron oxide hydrates with a boron halide within the fractionation zone, and the complex is removed from the fractionation zone dissolved in a distillate stream comprising benzene; and,
   d. the distillate stream is passed through a bed of a solid adsorbent which is periodically replaced and which removes the complex from the distillate stream, the improvement in the method of replacing the solid adsorbent which comprises drying the solid adsorbent with a vapor stream formed by vaporizing and superheating liquid removed from the bottom of the benzene drying column, and then returning the vapor stream to the benzene drying column and using the vapor stream as stripping vapor.

7. A method of drying a solid adsorbent used to treat a recycle benzene stream in a process for the alkylation of benzene wherein an alkylation zone effluent is formed by reacting benzene with ethylene in the presence of a boron halide promoted catalyst and the recycle benzene stream is formed by fractionating the alkylation zone effluent in a first fractionation column, which method comprises the steps of:
   a. withdrawing a hydrocarbon stream comprising monoalkylated and polyalkylated benzenes from the first fractionation column and passing the hydrocarbon stream into a second fractionation column;
   b. withdrawing a liquid stream comprising a polyalkylated benzene from the second fractionation column, and effecting the formation of a vapor stream by vaporizing the liquid stream;
   c. superheating the vapor stream;
   d. contacting the solid adsorbent with the vapor stream and effecting the drying of the solid adsorbent; and,
   e. injecting the vapor stream into the second fractionation column at a point above the lowest distillation tray contained within the second fractionation column.

* * * * *